United States Patent [19]

Hutchinson et al.

[11] Patent Number: 5,789,421
[45] Date of Patent: Aug. 4, 1998

[54] FIBRINOGEN RECEPTOR ANTAGONIST

[75] Inventors: John H. Hutchinson, Philadelphia; Wasyl Halczenko, Lansdale, both of Pa.

[73] Assignee: Merck & Co., Inc., Rahway, N.J.

[21] Appl. No.: 735,844

[22] Filed: Oct. 23, 1996

Related U.S. Application Data

[60] Provisional application No. 60/005,890 Oct. 26, 1995.

[51] Int. Cl.[6] .................. A61K 31/445; C07D 401/12
[52] U.S. Cl. .................................. 514/323; 546/201
[58] Field of Search .......................... 546/201; 514/323

[56] References Cited

U.S. PATENT DOCUMENTS

| | | | |
|---|---|---|---|
| 4,064,255 | 12/1977 | Champseix et al. | 424/267 |
| 4,122,255 | 10/1978 | Krapcho | 542/421 |
| 4,243,807 | 1/1981 | Friebe et al. | 546/232 |
| 4,622,331 | 11/1986 | Jozic | 514/331 |
| 5,030,654 | 7/1991 | Barnish et al. | 514/510 |
| 5,064,814 | 11/1991 | Klein et al. | 514/18 |
| 5,227,490 | 7/1993 | Hartman et al. | 514/317 |
| 5,559,127 | 9/1996 | Hartman | 514/322 |

FOREIGN PATENT DOCUMENTS

| | | |
|---|---|---|
| 0 352 249 | 1/1990 | European Pat. Off. . |
| 0 372 486 | 6/1990 | European Pat. Off. . |
| 0 381 033 | 8/1990 | European Pat. Off. . |
| 0 384 362 | 8/1990 | European Pat. Off. . |
| 0 405 537 | 1/1991 | European Pat. Off. . |
| 0 478 328 | 4/1992 | European Pat. Off. . |
| 0 478 362 | 4/1992 | European Pat. Off. . |
| 0 478 363 | 4/1992 | European Pat. Off. . |
| 0 479 481 | 4/1992 | European Pat. Off. . |
| 94/08962 | 4/1994 | WIPO . |

OTHER PUBLICATIONS

Ford–Hutchinson AW et al. Can. J. Physiol. Pharmacol. 67, 989–993, 1989.

*Primary Examiner*—Alan L. Rotman
*Assistant Examiner*—Evelyn Huang
*Attorney, Agent, or Firm*—Richard S. Parr; Melvin Winokur

[57] ABSTRACT

A fibrinogen receptor antagonist which is 5-[(4-Piperidinyl)methoxy]-2-indolecarbonyl-2(S)-phenylsulfonyl-amino-β-alanine.

10 Claims, 1 Drawing Sheet

FIBRINOGEN RECEPTOR ANTAGONIST

This application claims the benefit of U.S. Provisional application Ser. No. 60/005890, filed Oct. 26, 1995.

BACKGROUND OF THE INVENTION

The invention relates generally to modulating cell adhesion and to inhibiting the binding of fibrinogen and other proteins to blood platelets, and inhibiting the aggregation of blood platelets specifically to the gp IIb/IIIa fibrinogen receptor site. Fibrinogen is a glycoprotein present in blood plasma that participates in platelet aggregation and in fibrin formation. Platelets are cell-like anucleated fragments, found in the blood of all mammals, that also participate in blood coagulation. Interaction of fibrinogen with the IIb/IIIa receptor site is known to be essential for normal platelet function.

When a blood vessel is damaged by an injury or other causative factor, platelets adhere to the disrupted subendothethial surface. The adherent platelets subsequently release biologically active constituents and aggregate. Aggregation is initiated by the binding of agonists, such as thrombin, epinephrine, or ADP to specific platelet membrane receptors. Stimulation by agonists results in exposure of latent fibrinogen receptors on the platelet surface, and binding of fibrinogen to the glycoprotein IIb/IIIa receptor complex.

Attempts have been made to use natural products and synthetic peptides to determine the mechanism of adhesion and platelet aggregation. For example, Rouslahti and Pierschbacher in *Science*, 238, 491–497 (1987), describe adhesive proteins such as fibronectin, vitronectin, osteopontin, collagens, thrombospondin, fibrinogen, and von Willebrand factor that are present in extracellular matrices and in blood. The proteins contain the tripeptide arginine-glycine-aspartic acid (RGD) as their glycoprotein IIb/IIIa recognition site. These arginine-glycine-aspartic acid containing tripeptides are recognized by at least one member of a family of structurally related receptors, integrins, which are heterodimeric proteins with two membrane-spanning subunits. The authors state that the conformation of the tripeptide sequence in the individual proteins may be critical to recognition specificity.

Cheresh in *Proc. Nat'l Acad. Sci. U.S.A.*, 84, 6471–6475, (1987), describes an Arg-Gly-Asp directed adhesion receptor expressed by human endothethial cells that is structurally similar to the IIb/IIIa complex on platelets but is antigenically and functionally distinct. This receptor is directly involved in endothelial cell attachment to fibrinogen, von Willebrand factor, and vitronectin.

Pierschbacher and Rouslahti, in *J. of Biol. Chem.*, 262, (36), 17294–17298 (1987) hypothesized that the Arg-Gly-Asp sequence alone would be a sufficient signal for receptor recognition and binding and that, therefore, the conformation of the tri-peptide sequence would be determinative. Various synthetic peptides were produced and the authors concluded that the sterochemical conformation of Arg-Gly-Asp as influenced by enantiomeric substitutions or additions to this sequence significantly influenced receptor-ligand interaction. The authors further showed that cyclization of a decapeptide by forming a disulfide bridge between nonterminal residues Pen and Cys, rendered the peptide much less effective at inhibiting attachment to fibronectin.

In *Proc. Nat'l Acad. Sci. U.S.A.*, 81, 5985–5988 (1984), the same authors describe tetrapeptide variants of the cell recognition site of fibronectin that retain attachment-promoting activity. Peptides having a tetrapeptide recognition site are described in U.S. Pat. Nos. 4,589,881 and 4,614,517. A number of large polypeptide fragments in the cell-binding domain of fibronectin have cell-attachment activity. For example, see U.S. Pat. Nos. 4,517,686, 4,661,111 and U.S. Pat. No. 4,578,079.

Ruggeri et al., *Proc. Nat'l Acad. Sci. U.S.A.*, 83, 5708–5712 (1986) explore a series of synthetic peptides designed in lengths to 16 residues, that contain RGD and a valine attached to the aspartic acid residue of RGD that inhibit fibrinogen binding to platelets. See also Koczewiak et al., *Biochem.* 23, 1767–1774 (1984); Ginsberg et al., *J. Biol. Chem.* 260(7), 3931–3936 (1985); and Haverstick et al., *Blood* 66(4), 946–952 (1985). Other inhibitors are disclosed in Eur. Pat. App. Nos. 275,748 and 298,820.

A number of low molecular weight polypeptide factors have been isolated from snake venom. These factors apparently have high affinity for the gp IIb/IIIa complex. For example, Huang et al., *J. Biol Chem.*, 262, 16157–16163 (1987); Huang et al., *Biochemistry*, 28, 661–666 (1989) describe the primary structu is a 72 amino acid polypeptide that contains the RGD subunit. Echistatin is another compound which has high affinity for the gp IIb/IIIa complex. This polypeptide contains 49 amino acids and has the RGD subunit and various disulfide bridges. Gan et al., *J. Biol. Chem.*, 263, 19827–19832 (1988). See also, Dennis et al., *Proc. Nat'Acad. Sci. USA*, 87, 2471–2475 (1989). However, these snake venom factors also have high affinity for other members of the adhesive protein receptor family including the vitronectin and fibronectin receptors so are not selective for the gp IIb/IIIa complex.

While it is known that the tripeptide sequence Arg-Gly-Asp is present in certain polypeptides that can duplicate or inhibit the cell attachment-promoting effects of fibronectin and vitronectin, the tripeptide Arg-Gly-Asp has low activity. At present, there is little understanding of how other amino acids coupled to this sequence influence binding specificity. U.S. Pat. No 5,023,233, assigned to Merck & Co., Inc., discloses small cyclic hexapeptides which contain the sequence Arg-Gly-Asp and are useful platelet aggregation inhibitors. U.S. Pat. No. 5,037,808 discloses the use of indolyl platelet-aggregation inhibitors which are believed to act by antagonizing interactions between fibrinogen and/or extracellular matrix proteins and the platelet gp IIb/IIIa receptor. U.S. Pat. No. 5,037,808 discloses guanidino peptide mimetic compounds that retain an Asp residue which inhibit platelet aggregation. WO 9014103 describes the use of antibody-poly-peptide conjugates wherein said polypeptides contain the Arg-Gly-Asp (RGD) sequence.

WO 9111458 discloses the use of large cyclic peptides containing RGD flanked by proline residues which are platelet aggregation inhibitors. WO 9101331 discloses small cyclic platelet aggregation inhibitors which are synthetic cyclic pentapeptides containing the tripeptide sequence Arg-Gly-Asp and a thioether linkage in the cycle. Hartman et al., WO 9408962 discloses compounds which are effective for inhibiting platelet aggregation by inhibiting fibrinogen binding to the gp IIb/IIIa receptor site, e.g., 5-[2-(4-Piperidinyl)ethyloxy]-2-indolecarbonyl-2(S)-phenylsulfonylamino-β-alanine (compound II, FIG. 1B), and related compounds. U.S. Pat. No. 5,051,405 discloses the use of peptides and pseudopeptides such as N-amidino-piperidine-3-carboxylglycyl-L-aspartyl-L-valine that inhibit platelet aggregation and thrombus formation in mammalian blood. EP 445 796 discloses linear compounds which can include internal piperazinyl or piperidinyl derivatives. EP 437 367 discloses linear polypeptide fibrinogen receptor antagonists. U.S. Pat. No. 5,265,812 discloses compounds of the structure R$^1$—A—(W)$_a$—X—(CH$_2$)$_b$—(Y)$_c$—B—Z—COOR wherein R$^1$ is a guanidino or amidino moiety and A and B are chosen from specific monosubstituted aryl or heterocyclic moieties.

The present invention provides a novel fibrinogen receptor antagonist that has significant oral activity and is, therefore, useful for the reasons stated herein. The novel antagonist, which contains a methyleneoxy group, is significantly more potent than its next adjacent ethyleneoxy homolog. A number of serious diseases and disorders involve hyperthrombotic complications which lead to intravascular thrombi and emboli. Myocardial infarction, stroke, phlebitis and a number of other serious conditions create the need for novel and effective fibrinogen receptor antagonists.

SUMMARY OF THE INVETION

The invention is the fibrinogen receptor antagonist 5-[(4-Piperidinyl)methoxy]-2-indolecarbonyl-2(S)-phenylsulfonylamino-β-alanine (compound 26 in Scheme 2, also referenced in FIG. 1A as compound I) and pharmaceutically acceptable salts, racemates and racemic mixtures thereof, hydrates and polymorphs, hereinafter referred to as active drug.

Active drug of the invention is useful for inhibiting the binding of fibrinogen to blood platelets and for inhibiting the aggregation of blood platelets. The above-mentioned active drug can be used in a method of acting upon a fibrinogen receptor which comprises administering a therapeutically effective but non-toxic amount of such compound to a mammal, preferably a human. A pharmaceutical composition comprising a pharmaceutically acceptable carrier and, dispersed therein, an effective but non-toxic amount of active drug is another feature of this invention.

DETAILED DESCRIPTION OF THE INVENTION

The fibrinogen receptor antagonist compound of the present invention 5-[(4-Piperidinyl)methoxy]-2-indolecarbonyl-2(S)-phenylsulfonylamino-β-alanine, and pharmaceutically acceptable salts thereof, racemates, racemic mixtures, hydrates and polymorphs, is useful as an orally active compound for inhibiting the binding of fibrinogen to blood platelets and for inhibiting the aggregation of blood platelets. The compound 5-[(4-Piperidinyl)methoxy]-2-indolecarbonyl-2(S)-phenylsulfonylamino-β-alanine is nearly twice as orally active as the next adjacent homolog 5-[2-(4-Piperidinylethyl)oxy]-2-indolecarbonyl-2(S)-phenylsulfonylamrino-β-alanine.

One test which is used to evaluate fibrinogen receptor antagonist activity is based on evaluation of inhibition of ADP-stimulated platelets. Aggregation requires that fibrinogen bind to and occupy the platelet fibrinogen receptor site. Inhibitors of fibrinogen binding inhibit aggregation. In the ADP-stimulated platelet aggregation assay used to determine inhibition associated with the compounds claimed in the instant invention, human platelets are isolated from fresh blood, collected into acid citrate/dextrose by differential centrifugation followed by gel filtration on Sepharose 2B in divalent ion-free Tyrode's buffer (pH 7.4) containing 2% bovine serum albumin.

Platelet aggregation is measured at 37° C. in a Chronolog aggregometer. The reaction mixture contains gel-filtered human platelets (2×10$^8$ per ml), fibrinogen (100 micrograms per ml (ug/ml)), Ca$^2$+(1 mM), and the compound to be tested. The aggregation is initiated by adding 10 mM ADP 1 minute after the other components are added. The reaction is then allowed to proceed for at least 2 minutes. The extent of inhibition of aggregation is expressed as the percentage of the rate of aggregation observed in the absence of inhibitor. The IC$_{50}$ is the dose of a particular compound inhibiting aggregation by 50% relative to a control lacking the compound.

According to the in vitro analysis, 5-[(4-Piperidinyl)methoxy]-2-indolecarbonyl-2(S)-phenylsulfonylamino-β-alanine has approximately the same binding ability as 5-[2-(4-Piperidinylethyl)oxy]-2-indolecarbonyl-2(S)-phenylsulfonylamino-β-alanine. However, ex vivo studies designed to evaluate the in vivo efficacy of fibrinogen receptor antagonists show that 5-[(4-Piperidinyl)methoxy]-2-indolecarbonyl-2(S)-phenylsulfonylamino-β-alanine is nearly twice as effective as 5-[2-(4-Piperidinylethyl)oxy]-2-indolecarbonyl-2(S)-phenylsulfonylamino-β-alanine. This substantial distinction translates into valuable cost, convenience and therapeutic advantages for patients using 5-[(4-Piperidinyl)methoxy]-2-indolecarbonyl-2(S)-phenylsulfonyl-amino-β-alanine to inhibit platelet aggregation.

Figure 1A:
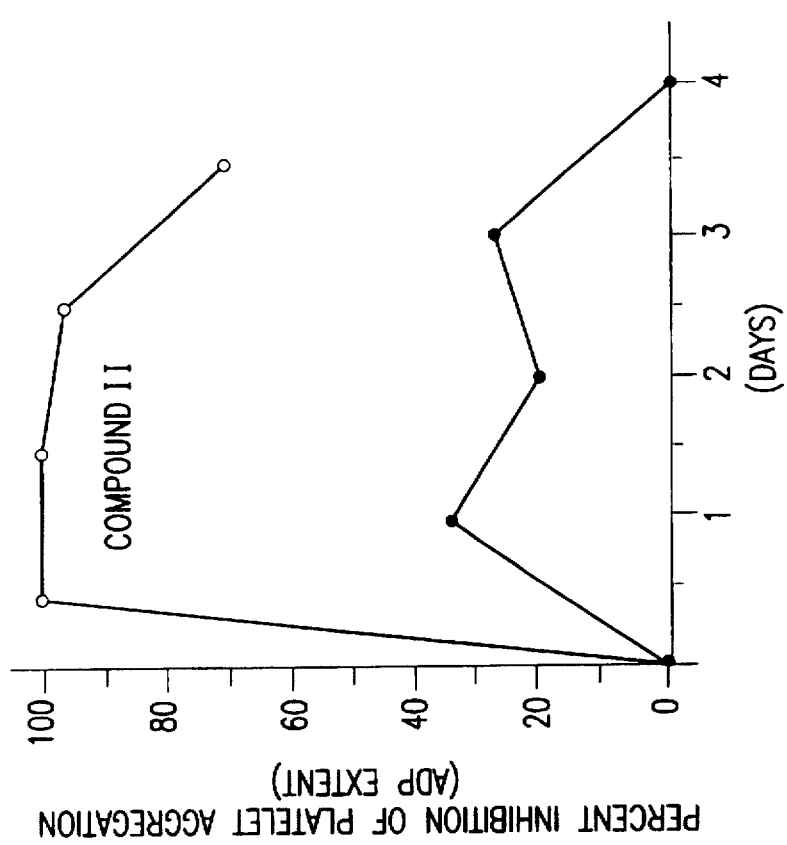
FIG. 1A shows percent inhibition of platelet aggregation of compound 2-6("compound I"), which is 5-[(4-Piperidinyl)methoxy]-2-indolecarbonyl-2(S )-phenyl sulfonyl-amino-β-alanine.
Figure 1B:
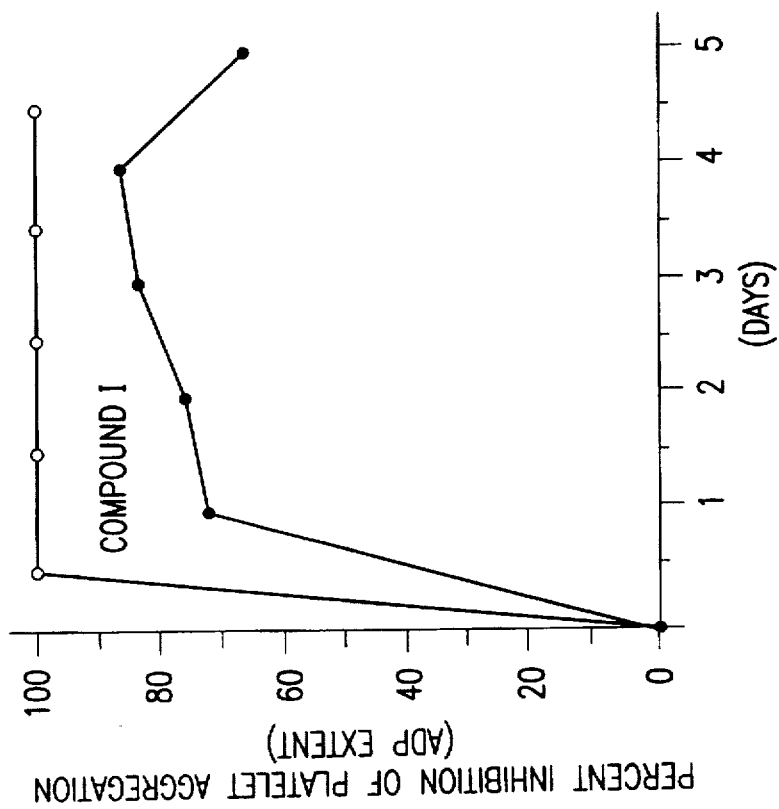
FIG. 1B shows percent inhibition of platelet aggregation of "compound II," which is 5-[(4-Piperidinyl)ethyloxy]-2-indolecarbonyl-2(S)-phenylsulfonyl-amino-β-alanine.

In the procedure for determining potency of fibrinogen receptor antagonist following oral administration to a patient, tested compound is orally administered daily to a rhesus monkey. Blood samples are drawn 30 minutes prior to daily dose administration (data points represented on FIG. 1 by a filled circle) and 3 hours after daily dose administration (data points represented on FIG. 1 by an open circle) and subjected to the ADP-stimulated platelet aggregation assay.

The results clearly show that compound I is nearly twice as potent following oral administration than compound 1. 0.3 mg/kg/day p.o. of compound I was administered to one monkey and 0.5 mg/kg/day p.o. of compound II was administered to another monkey. The results show that after one day, just prior to the second day dose, compound I provided more than 70% inhibition of platelet aggregation, while compound II provided less than 40% inhibition of platelet aggregation.

The term "pharmaceutically acceptable salts" shall mean non-toxic salts of the compounds of this invention which are generally prepared by reacting the free base with a suitable organic or inorganic acid. Representative salts include the following salts: acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynapthoate, iodide, isothionate, lactate, lactobionate, laurate, malate, maleate, mandelate, mesylate, methylbromide, methylnitrate, methylsulfate, mucate, napsylate, nitrate, oleate, oxalate, pamaote, palmitate, panthothenate, phosphate/diphosphate, polygalacturonate, salicylate, stearate, subacetate, succinate, tannate, tartrate, teoclate, tosylate, triethiodide, valerate.

5-|(4-Piperidinyl)methoxy|-2-indolecarbonyl-2(S)-phenylsulfonylamino-β-alanine is a chiral compound. Included within the scope of the present invention are racemic mixtures and separated enantiomers of 5-|(4-Piperidinyl)methoxy|-2-indolecarbonyl-2(S)-phenylsulfonylamino-β-alanine. Furthermore, hydrates as well as anhydrous compositions and polymorphs of the general formula are within the present invention. The term "active drug" includes 5-|(4-Piperidinyl)methoxy|-2-indolecarbonyl-2(S)-phenylsulfonylamino-β-alanine and its salts, racemic mixtures or separated enantiomers, hydrates or anhydrous forms, polymorphs, and pharmaceutically acceptable salts.

Prodrugs, such as ester derivatives of active drug are compound derivatives which, when absorbed into the bloodstream of a warm-blooded animal, cleave in such a manner as to release the drug form and permit the drug to afford improved therapeutic efficacy.

The term "pharmaceutically effective amount" shall mean that amount of a drug or pharmaceutical agent that will elicit the biological or medical response of a tissue, system or animal that is being sought by a researcher or clinician. The term "anti-coagulant" shall include heparin, and warfarin. The term "thrombolytic agent" shall include agents such as streptokinase and tissue plasminogen activator. The term "platelet anti-aggregation agent" shall include agents such as aspirin and dipyridamole.

In the schemes and examples below, various reagent symbols have the following meanings:
BOC (or Boc): t-butyloxycarbonyl
Pd-C: Palladium on activated carbon catalyst
DMF: Dimethylformamide
DMSO: Dimethylsulfoxide
CBZ: Carbobenzyloxy
$CH_2Cl_2$: Methylene chloride
$CHCl_3$: chloroform
EtOH: ethanol
MeOH: methanol
EtOAc: ethyl acetate
HOAc: acetic acid
BOP: Benzotriazol-1-yloxytris(dimethylamino)phosphonium, hexafluorophosphate
EDC: 1-(3-Dimethylaminopropyl)-3-ethylcarbodiimide hydrochloride
Oxone: potassium peroxymonosulfate
LDA: Lithium diisopropylamide Active drug can be administered in such oral forms as tablets, capsules (each of which includes sustained release or timed release formulations), pills, powders, granules, elixirs, tinctures, suspensions, syrups, and emulsions. Likewise, it may be administered in intravenous (bolus or infusion), intraperitoneal, subcutaneous, or intramusculsar form, all using forms well known to those of ordinary skill in the pharmaceutical arts. An effective but non-toxic amount of active drug can be employed as an anti-aggregation agent.

Active drug may be administered to patients where prevention of thrombosis by inhibiting binding of fibrinogen to the platelet membrane glycoprotein complex IIb/IIIa receptor is desired. It is useful in surgery on peripheral arteries (arterial grafts, carotid endarterectomy) and in cardiovascular surgery where manipulation of arteries and organs, and/or the interaction of platelets with artificial surfaces, leads to platelet aggregation and consumption. The aggregated platelets may form thrombi and thromboemboli. Active drug may be administered to these surgical patients to prevent the formation of thrombi and thromboemboli.

Extracorporeal circulation is routinely used for cardiovascular surgery in order to oxygenate blood. Platelets adhere to surfaces of the extracorporeal circuit. Adhesion is dependent on the interaction between gp IIb/IIIa on the platelet membranes and fibrinogen adsorbed to the surface of the circuit. (Gluszko et al., *Amer. J. Physiol.*, 252(H), 615–621 (1987)). Platelets released from artificial surfaces show impaired hemostatic function. Active drug may be administered to prevent adhesion.

Other applications of active drug include prevention of platelet thrombosis, thromboembolism and reocclusion during and after thrombolytic therapy and prevention of platelet thrombosis, thromboembolism and reocclusion after angioplasty or coronary artery bypass procedures. It may also be used to prevent myocardial infarction.

The dosage regimen utilizing active drug is selected in accordance with a variety of factors including type, species, age, weight, sex and medical condition of the patient; the severity of the condition to be treated; the route of administration; the renal and hepatic function of the patient; and the particular compound or salt thereof employed. An ordinarily skilled physician or veterinarian can readily determine and prescribe the effective amount of the drug required to prevent, counter, or arrest the progress of the condition.

Oral dosages of active drug when used for the indicated effects, will range between about 0.005 mg per kg of body weight per day (mg/kg/day) to about 50 mg/kg/day and preferably 0.005–20 mg/kg/day and most preferably 0.005–10 mgkg/day. Intravenously, the most preferred doses will range from about 0.5 to about 5 mg/kg/minute during a constant rate infusion. Active drug may be administered in one or divided doses of two, three, or four times daily. Furthermore, active drug can be administered in intranasal form via topical use of suitable intranasal vehicles, or via transdermal routes, using those forms of transdermal skin patches well known to those of ordinary skill in that art. To be administered in the form of a transdermal delivery system, the dosage administration will, or course, be continuous rather that intermittent throughout the dosage regime.

In the methods of the present invention, the active drug can form the active ingredient, and is typically administered in admixture with suitable pharmaceutical diluents, excipients or carriers (collectively referred to herein as "carrier" materials) suitably selected with respect to the intended form of administration, that is, oral tablets, capsules, elixirs, syrups and the like, and consistent with convention pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl cellulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water and the like. Moreover, when desired or necessary, suitable binders, lubricants, distintegrating agents and coloring agents can also be incorporated into the mixture. Suitable binders include starch, gelatin, natural sugars such as glucose or beta-lactose, corn-sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrators include, without limitation, starch methyl cellulose, agar, bentonite, xanthan gum and the like.

The active drug can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

Active drug may also be delivered by the use of monoclonal antibodies as individual carriers to which the compound molecules are coupled. Active drug may also be coupled with soluble polymers as targetable drug carriers. Such polymers can include polyvinyl-pyrrolidone, pyran copolymer, polyhydroxy-propyl-methacrylamidephenol, polyhydroxy-ethyl-aspartamide-phenol, or polyethyleneoxide-polylysine substituted with palmitoyl residues. Furthermore, active drug may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacrylates and cross linked or amphipathic block copolymers of hydrogels.

Active drug can also be co-administered with suitable anticoagulation agents or thrombolytic agents such as plasminogen activators or streptokinase to achieve synergistic effects in the treatment of various vascular pathologies. They may also be combined with heparin, aspirin, or warfarin.

5-[(4-Piperidinyl)methoxy]-2-indolecarbonyl-2(S)-phenylsulfonylamino-β-alanine was prepared according to the procedure of the following example. Those skilled in the art will readily understand that known variations of the conditions and processes of the following preparative procedures can be used to prepare these compounds. All temperatures are degrees Celsius unless otherwise noted.

SCHEME 1

2-Substituted-3-Aminopropionates are prepared in the following manner:

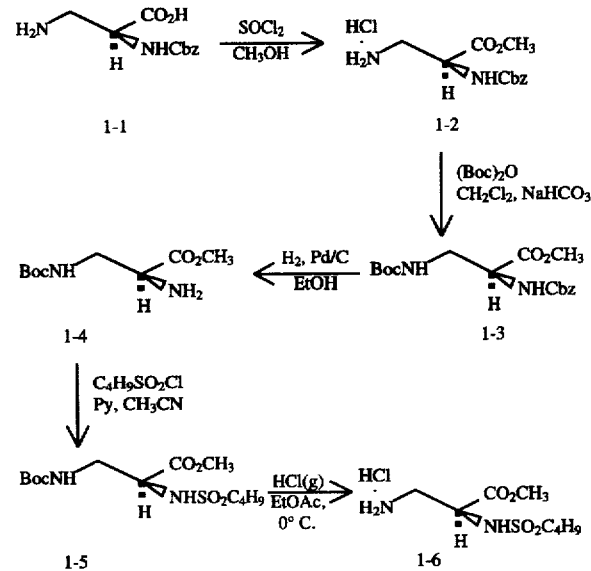

Methyl 2(S)-benzyloxycarbonylamino-3-aminopropionate hydrochloride (1-2)

To a cooled suspension of 2(S)-benzyloxycarbonylamino-3-aminopropionic acid (Fluka) (1-1) (10 g, 0.042 mol) in 150 ml of methanol was added 5.47 g (0.046 mol) of thionyl chloride over 20 minutes. The resulting solution was allowed to stir at room temperature overnight. After-18 hrs, the solvent was removed in vacuo, and the residual solid was stirred with 150 ml of ether for 0.5 hr. The resulting white solid was collected and air dried to give 1-2.

$^1$H NMR (300 MHz, CD$_3$OD) δ 3.26 (2H, m), 3.45 (1H, dd), 3.77 (3H, s), 4.25 (1H, m), 5.13 (2H, s), 7.37 (5H, m).

Methyl 2(S)-benzyloxycarbonylamino-3-(N-t-butyloxycarbonyl)-aminopropionate (1-3)

To a 2-phase mixture of CH$_2$Cl$_2$ (500 ml) and saturated NaHCO$_3$ solution (300 ml) was added 28.87 g (0.10 mol) of 1-2. After a few minutes, 21.83 g (0.10 mol) of di-t-butyldicarbonate was added in one portion and the resulting mixture was stirred at room temperature for 4 hrs. The CH$_2$Cl$_2$ layer was then separated from the aqueous layer, and the aqueous layer was extracted with 300 ml of CH$_2$Cl$_2$. The combined organic extracts were washed with brine, dried and the solvent removed in vacuo to provide the product as a viscous oil. Trituration of this oil with 300 ml of hexane gave 1-3 as a white solid, m.p. 85°–87°.

$^1$H NMR (300 MHz, CDCl$_3$) δ 1.42 (9H; s), 1.50 (4H, m), 1.62 (1H, m), 3.52 (2H, m), 3.75 (3H, s), 4.41 (1H, m), 4.83 (1H, m), 5.12 (2H, s), 5.78 (1H, m), 7.35 (5H, m).

Methyl 2(S)-amino-3-(N-t-butyloxycarbonyl)aminopropionate (1-4)

To a solution of 6.60 g (0.0187 mol) 1-3 in 150 ml EtOH was added 0.5 g of 10% Pd/C. The resulting mixture was hydrogenated under balloon pressure at room temperature for 4 hrs. The catalyst was filtered off and the solvent removed in vacuo to provide 1-4 as a viscous oil.

$^1$H NMR (300 MHz, CDCl$_3$) δ 1.45 (9H, s), 1.49 (2H, m), 1.59 (2H, m), 3.25 (1H, m), 3.49 (1H, m), 3.58 (1H, m), 3.75 (3H, s), 5.03 (1H, m).

Methyl 2(S)-butylsulfonylamino-3-(N-t-butyloxycarbonyl)amino-propionate (1-5)

To a solution of 0.400 g (0.00183 mol) of 1-4 in 10 ml of CH$_3$CN was added 0.226 g (0.00286 mol) pyridine followed by 0.408 g (0.0026 mol) of n-butanesulfonyl chloride. The resulting solution was stirred at room temperature for 2.5 hrs at which time starting material was consumed. The solvent was removed in vacuo and 50 ml of H$_2$O added to the residual material. This mixture was extracted with 3×50 ml portions of ethyl acetate and the combined extracts washed with brine, dried (Na$_2$SO$_4$), filtered and concentrated to give 0.5 g of a viscous oil. Trituration to this oil with 25 ml of hexane provided 1-5 as a white, amorphous solid.

$^1$H NMR (300 MHz, CDCl$_3$) δ 0.95 (3H, t), 1.43 (9H, s), 1.48 (2H, m), 1.80 (2H, m), 3.03 (2H, m), 3.52 (2H, t), 3.80 (3H, s), 4.22 (1H, m), 4.99 (1H, bt), 5.48 (1H, bd).

Methyl 2(S)-butylsulfonylamino-3-aminopropionate hydrochloride (1-6)

A cooled (−20° C.) solution of 0.400 g (0.00118 mol) of 1-5 in 25 ml of ethyl acetate was treated with HCl gas for 15 min. The resulting solution was then stoppered and allowed to stir at 0° C. for an additional hour. The solvent and excess HCl were removed in vacuo to give 1-6 as a hygroscopic, yellowish foam.

$^1$H NMR (300 MHz, CDCl$_3$) δ 0.94 (3H, t), 1.44 (9H, s), 1.48 (2H, m), 1.80 (2H, m), 3.04 (2H, m), 3.53 (2H, bt), 3.80 (3H, s), 4.22 (1H, m), 4.93 (1H, m), 5.40 (1H, bd).

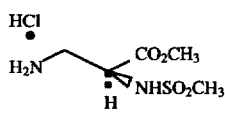

Methyl 2(S)-Methylsulfonylamino-3-aminopropionate hydrochloride (1-7)

1-7 was prepared as described above for the butylsulfonylamino analog (1-6) using methanesulfonyl chloride at the appropriate stage.

$^1$H NMR (300 MHz, CD$_3$OD) δ 3.07 (3H, s), 3.13 (1H, m), 3.43 (1H, dd), 3.83 (3H, s), 4.96 (1H, m).

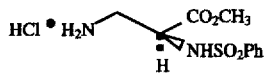

Methyl 2(S)-Phenylsulfonylamino-3-aminopropionate hydrochloride (1-8a)

1-8a was prepared as described above for 1-6 using phenylsulfonylchloride at the appropriate stage.

$^1$H NMR (300 MHz, D$_2$O) δ 3.22 (1H, t), 3.45 (3H, S), 3.51 (2H, m), 4.44 (1H, m), 7.61–7.80 (3H, m), 7.92 (2H, m).

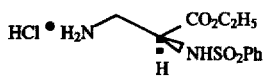

Ethyl 2(S)-Phenylsulfonylamino-3-aminopropionate hydrochloride (1-8b)

1-8b was prepared as described above for 1-8a using ethanol rather than methanol in the conversion of 1-1 to 1-2.

$^1$H NMR (300 MHz, CD$_3$OD) δ 1.0 (3H, t), 3.05 (1H, m), 3.35 (1H, dd), 3.9 (2H, q), 4.25 (1H, m), 7.5–7.7 (3H, m), 7.9 (2H, m).

SCHEME 2

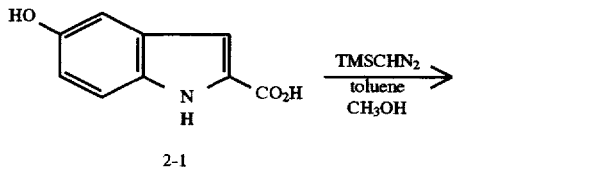

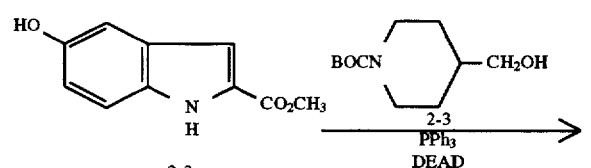

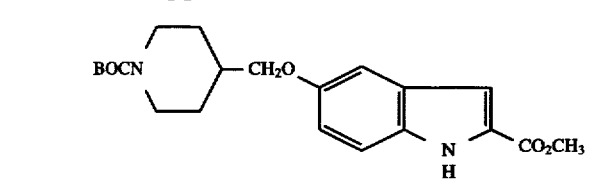

-continued
SCHEME 2

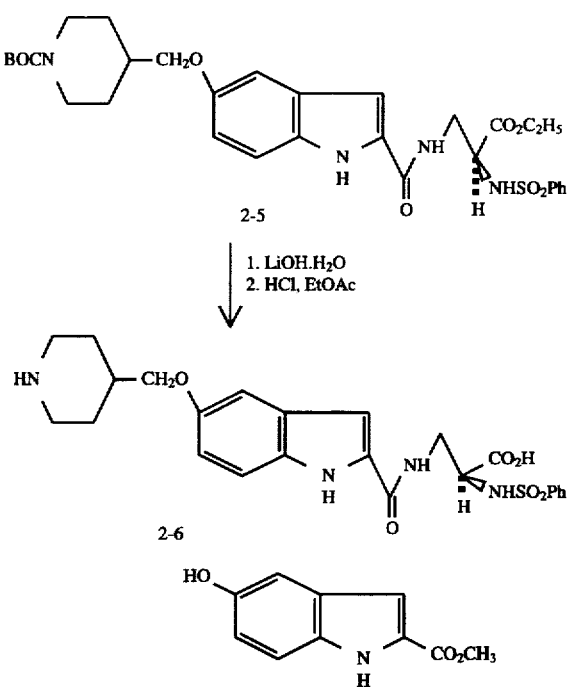

5-Hydroxy-2-indolecarboxylic acid methyl ester (2-2)

5-Hydroxyindole-2-carboxylic acid (Aldrich) (3.54 g, 0.02 mol) in toluene (100 ml)/methanol (25 ml) was treated with TMSCHN$_2$ (0.022 mol) and this solution was stirred at room temperature for 16 hours. The solvent was removed and the residue purified by flash chromatography on silica gel eluting with CHCl$_3$ (95)/MeOH(5) to give pure 2-2. R$_f$ 0.3, silica, CHCl$_3$ (95)/MeOH(5).

$^1$H NMR (300 MH$_3$, CDCl$_3$) δ 3.94 (3H, S), 4.79 (1H, S), 6.94 (1H, dd), 7.09 (2H, m), 7.28 (1H, m), 8.82 (1H, b).

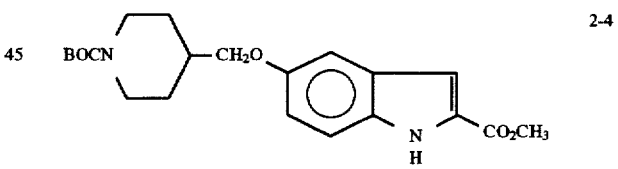

5-[(4-N-Boc-Piperidinyl)methoxy]-2-indolecarboxylic acid methyl ester (2-4)

A solution of 2-2 (0.96 g, 5 mmol) in THF (15 ml) was treated with PPh$_3$ (1.48 g, 5.5 mmol) and after stirring for 10 minutes, diethyl azodicarboxyate (DEAD) (0.96 g, 5.5 mmol) and 2-3 (1.15 g, 5 mmol) in THF (10 ml) was added dropwise over 1 hour. After stirring at room temperature for 16 hours, the solvent was removed and the residue was taken up in EtOAc, washed with H$_2$O, saturated NaHCO$_3$, brine, 10% KHSO$_4$, brine and dried (Na$_2$SO$_4$). The solvent was removed and the residue purified by flash chromatography on silica gel eluting with hexane(4)/EtOAc(1) to give pure 2-4. R$_f$ 0.21 silica, 20% EtOAc/hexane.

$^1$H NMR (300 MHz, CDCl$_3$) δ1.20–1.32 (3H, m), 1.42 (9H, s), 1.81–1.90 (2H, m), 2.70–2.85 (2H, m), 3.84 (2H, d), 3.94 (3H, s), 4.09–4.14 (2H, m), 7.00 (1H, dd), 7.06 (1H, m), 7.13 (1H, m), 7.32 (1H, d), 8.82 (1H, s).

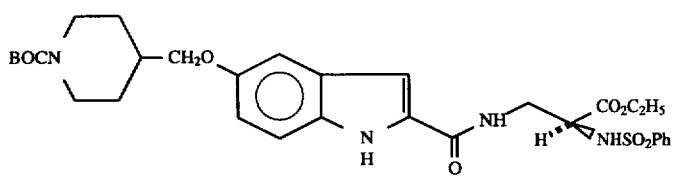

5-[(4-N-Boc-Piperidinyl)methoxy]-2-indolecarbonyl-2(S)-phenyl-sulfonylamino-β-alanine ethyl ester (2-5)

2-4 (0.77 g, 1.9 mmol) was treated with LiOH.H₂O (0.24 g, 5.7 mmol) stirring for 1 hour at room temperature to give the desired acid. $R_f$ 0.5, silica, CHCl₃ (95)/MeOH(5).

This acid (0.226 g, 0.58 mmol) was dissolved in DMF and a room temperature was treated successively with 1-8b (0.17 g, 5.8 mmol), HOBT (0.086 g, 0.64 mmol), NMM (0.176 g, 1.74 mmol), and EDC (0.13 g, 0.68 mmol). After stirring for 24 hours, the solvent was removed and the residue was taken up in H₂O (50 ml)/EtOAc(100 ml) and this organic phase was washed with 10% KHSO₄, brine, saturated NaHCO3, brine and dried (Na₂SO₄). The solvent was removed and the residue purified by flash chromatography on silica gel eluting with CHCl3(95)/MeOH(5) to give pure 2-5; $R_f$ 0.19 silica, 60% EtOAc/hexane.

¹H NMR (300 MHz, CDCl₃) δ 1.15 (3H, t), 1.23–1.39 (3H, m), 1.48 (9H, s), 1.81–1.91 (2H, m), 2.70–2.83 (2H, m), 3.65–3.76 (1H, m), 3.85 (2H, d), 3.89–3.98 (1H, m), 4.01–4.25 (5H, m), 5.80 (1H, m), 6.78 (1H, m), 6.72 (1H, s), 6.96 (1H, m), 7.04 (1H, s), 7.42–7.61 (4H, m), 7.85 (2H, d), 9.00 (1H, s).

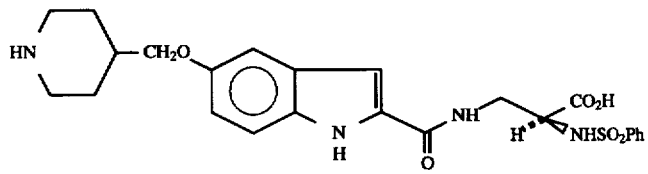

5-[(4-Piperidinyl)methoxy]-2-indolecarbonyl-2(S)-phenylsulfonyl-amino-β-alanine (2-6)

2-5 (0.33 g, 0.53 mmol) was treated with LiOHH₂O(0.066 g, 1.57 mmol) stirring for one hour at room temperature to provide the desired acid. $R_f$ 0.1, silica CHCl3 (95)/CH₃₀H (5)/HOAc(1).

This acid was dissolved in EtOAc, cooled to −25° and treated with HCl gas for 15 minutes and then stirred at 0° C. for 1 hour. The solvent was removed and the residue was triturated with EtOAc to give pure 2-6.

¹H NMR (400 MHz, CD₃OD) δ 1.60–1.71 (2H, m), 2.10–2.22 (3H, m), 2.99–3.11 (2H, m), 3.42–3.50 (2H, m), 3.54 (1H, dd), 3.72 (1H, dd), 3.95 (2H, d), 4.12 (1H, dd), 6.88 (1H, s), 6.90 (1H, dd), 7.08 (1H, d), 7.30–7.40 (4H, m), 7.52–7.59 (1H, m), 7.61-7.70 (1H, m), 7.78–7.86 (H, m).

Preparation of 2-3

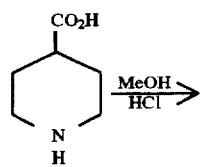

-continued
Preparation of 2-3

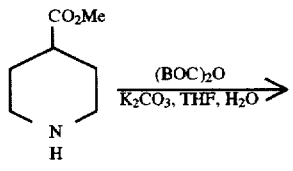

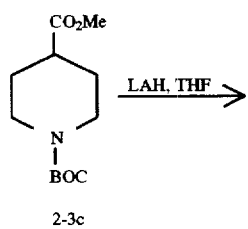

-continued
Preparation of 2-3

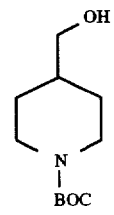

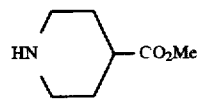

Isonipecotic acid methyl ester 2-3b

Isonipecotic acid 2-3a (25 g, 0.19 mol; Aldrich) was suspended in MeOH (300 mL) at room temperature and HCl gas was bubbled through until saturated and a clear solution was obtained. After a further 10 minutes, the solvent was removed in vacuo to provide 2-3b as a solid (HCl salt).

$^1$H NMR (300 MHz, CD3OD) δ: 1.9 (2H, m), 2.18 (2H, m), 2.78 (1H, m), 3.12 (2H, br t), 3.40 (2H, m), 3.74 (3H, s).

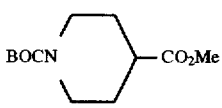

2-3c

N-Boc-Isonipecotic acid methyl ester 2-3c

To a solution of isonipecotic acid methyl ester HCl (2-3b) (34 g, 0.19 mol), and di-tert-butyl dicarbonate (43.5 g, 0.2 mol) in THF (300 mL) and H$_2$O (150 mL) was added-K$_2$CO$_3$ (28.8 g, 0.21 mol). After 4 hours, the mixture was poured into water, extracted with EtOAc then washed with brine, dried (MgSO$_4$) and evaporated to give the title compound 2-3c as an oil with a small amount of di-tert-butyl dicarbonate.

$^1$H NMR (300 MHz, CDCl$_3$) δ: 1.45 (9H, s), 1.65 (2H, m), 1.86 (2H, m), 2.45 (1H, m), 2.82 (2H, br t), 3.70 (3H, s), 4.00 (2H, m).

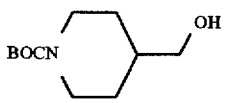

2-3

N-Boc-4-Piperidinyl methanol 2-3

LAH (3.8 g, 100 mmol) was added portionwise to a solution the ester 2-3c (20.3 g, 83.5 mmol) in THF (300 mL) at 0° C. under argon. After the addition was complete, the mixture was stirred for 2 hours then poured onto ice. IN HCl was added and the slurry extracted 3× EtOAc. The organic layer was washed with water then brine, dried (MgSO$_4$) and concentrated to give a white solid. The solid was swished with hexane/ether 9:1 and filtered to provide the alcohol 2-3.

$^1$H NMR (300 MHz, CDCl$_3$) δ: 1.13 (2H, dq), 1.46 (9H, s), 1.6–1.8 (3H, m), 1.89 (1H, s), 2.68 (2H, br t), 3.45 (2H, d), 4.10 (2H, m).

Therapeutic Treatment

Compounds of the invention may be administered to patients where inhibition of human or mammalian platelet aggregation or adhesion is desired.

Compounds of the invention are useful in inhibiting platelet aggregation and thus, they may find utility in surgery on peripheral arteries (arterial grafts, carotid endaterectomy) and in cardiovascular surgery where manipulation of arteries and organs, and/or the interation of platelets with artificial surfaces, leads to platelet aggregation and consumption. The aggregated platelets may form thrombi and thromboemboli. Compounds of the invention may be administered to these surgical patients to prevent the formation of thrombi and thromboemboli.

EXAMPLE 3

Tablet Preparation

Tablets containing 25.0, 50.0, and 100.0 mg., respectively, of the active compound 5-[(4-Piperidinyl)methoxy]-2-indolecarbonyl-2(S)-phenylsulfonylamino-β-alanine are prepared as illustrated below:

TABLE FOR DOSES CONTAINING FROM 25–100 MG OF THE ACTIVE COMPOUND

|  | Amount-mg | | |
| --- | --- | --- | --- |
| Active Compound | 25.0 | 50.0 | 100.0 |
| Microcrystalline cellulose | 37.25 | 100.0 | 200.0 |
| Modified food corn starch | 37.25 | 4.25 | 8.5 |
| Magnesium stearate | 0.50 | 0.75 | 1.5 |

All of the active compound, cellulose, and a portion of the corn starch are mixed and granulated to 10% corn starch paste. The resulting granulation is sieved, dried and blended with the remainder of the corn starch and the magnesium stearate. The resulting granulation is then compressed into tablets containing 25.0, 50.0, and 100.0 mg, respectively, of active ingredient per tablet.

EXAMPLE 4

Intravenous formulations

An intravenous dosage form of the above-indicated active compound is prepared as follows:

| Active Compound | 0.5–10.0 mg |
| --- | --- |
| Sodium Citrate | 5–50 mg |
| Citric Acid | 1–15 mg |
| Sodium Chloride | 1–8 mg |
| Water for Injection (USP) | q.s. to 1 L |

Utilizing the above quantities, the active compound is dissolved at room temperature in a previously prepared solution of sodium chloride, citric acid, and sodium citrate in Water for Injection (USP, see page 1636 of United States Pharmacopeia/National Formulary for 1995, published by United States Pharmacopeial Convention, Inc., Rockville, Md., copyright 1994.

EXAMPLE 5

Intravenous formulation

A pharmaceutical composition was prepared at room temperature using 5-[(4-Piperidinyl)methoxy]-2-indolecarbonyl-2(S)-phenylsulfonylamino-β-alanine, a citrate buffer, and sodium chloride, to obtain a concentration of of 0.25 mg/ml.

800 grams of water was introduced into a standard pharmaceutical mixing vessel. 0.25 grams of 5-[(4-Piperidinyl)methoxy]-2-indolecarbonyl-2(S)-phenylsulfonylamino-β-alanine was dissolved in the water. 2.7 grams sodium citrate and 0.16 grams citric acid were added to obtain a finished citrate concentration of 10 mM. 8 grams of sodium chloride was added. 200 grams of water was then added to achieve the desired final concentrations of ingredients. The resulting aqueous formulation had the following concentrations:

| Ingredient | Amount |
| --- | --- |
| 5-[(4-Piperidinyl)methoxy]-2-indolecarbonyl-2(S)-phenylsulfonylamino-β-alanine | 0.25 mg/ml |
| citrate buffer | 10 mM |
| sodium chloride | 8 mg/ml |

The finished concentrated formulation is stored in a standard USP Type I borosilicate glass container at 30–40 degrees C. Prior to compound administration, the concentrated formulation is diluted in a 4:1 ratio resulting in a finished concentration of 0.05 mg/ml and transferred to an infusion bag.

What is claimed is:

1. A compound which is 5-[(4-Piperidinyl)methoxy]-2-indolecarbonyl-2(S)-phenylsulfonylamino-β-alanine and pharmaceutically acceptable salts thereof.

2. A compound of claim 1 which is 5-[(4-Piperidinyl)methoxy]-2-indolecarbonyl-2(S)-phenylsulfonylamino-β-alanine.

3. A composition for inhibiting the binding of fibrinogen to blood platelets in a mammal, comprising a therapeutically effective amount of a compound of claim 1 and a pharmaceutically acceptable carrier.

4. A composition for inhibiting the aggregation of blood platelets in a mammal, by blocking fibrinogen from acting at its receptor site, comprising a therapeutically effective amount of a compound of claim 1 and a pharmaceutically acceptable carrier.

5. A method for inhibiting the binding of fibrinogen to blood platelets in a mammal, comprising administering to the mammal a composition of claim 3.

6. A method for inhibiting the aggregation of blood platelets in a mammal, by blocking fibrinogen from acting at its receptor site, comprising administering to the mammal a composition of claim 4.

7. A composition for inhibiting the binding of fibrinogen to blood platelets, in a mammal, comprising a therapeutically effective amount of a compound of claim 2 and a pharmaceutically acceptable carrier.

8. A composition for inhibiting the aggregation of blood platelets, in a mammal, by blocking fibrinogen from acting at its receptor site, comprising a therapeutically effective amount of a compound of claim 2 and a pharmaceutically acceptable carrier.

9. A method for inhibiting the binding of fibrinogen to blood platelets in a mammal, by blocking fibrinogen from acting at its receptor site, comprising administering to the mammal a composition of claim 7.

10. A method for inhibiting the aggregation of blood platelets in a mammal, by blocking fibrinogen from acting at its receptor site, comprising administering to the mammal a composition of claim 8.

* * * * *